United States Patent
Fry

(10) Patent No.: US 6,365,670 B1
(45) Date of Patent: Apr. 2, 2002

(54) ORGANOPOLYSILOXANE GELS FOR USE IN COSMETICS

(75) Inventor: Bryan E. Fry, Tecumseh, MI (US)

(73) Assignee: Wacker Silicones Corporation, Adrian, MI (US)

( * ) Notice: Subject to any disclaimer, the term of this patent is extended or adjusted under 35 U.S.C. 154(b) by 0 days.

(21) Appl. No.: 09/522,480

(22) Filed: Mar. 10, 2000

(51) Int. Cl.$^7$ .............................. C08L 83/04; C08J 3/05; A61K 7/02
(52) U.S. Cl. ................. 524/862; 524/267; 524/268; 524/379; 524/385; 524/386; 524/588; 524/731; 524/860; 524/861; 524/864; 523/335; 514/844; 514/845; 514/846; 514/847; 514/848; 514/937; 424/59; 424/64; 424/65; 424/70.1
(58) Field of Search ............................... 524/267, 268, 524/379, 365, 386, 588, 731, 860, 861, 862, 864; 523/335; 514/844, 845, 846, 847, 848, 937; 424/57, 64, 65, 70.1

(56) References Cited

U.S. PATENT DOCUMENTS

| | | |
|---|---|---|
| 3,159,601 A | 12/1964 | Ashby |
| 3,159,662 A | 12/1964 | Ashby |
| 3,220,972 A | 11/1965 | Lamoreaux |
| 3,715,334 A | 2/1973 | Karstedt |
| 3,775,452 A | 11/1973 | Karstedt |
| 3,814,730 A | 6/1974 | Karstedt |
| 4,594,134 A | 6/1986 | Hanada et al. |
| 4,742,142 A | 5/1988 | Shimizu et al. |
| 4,806,430 A | 2/1989 | Spielvogel et al. |
| 4,970,252 A | 11/1990 | Sakuta et al. |
| 4,980,167 A | 12/1990 | Harashima et al. |
| 4,987,169 A | 1/1991 | Kawata et al. |
| 5,136,068 A | 8/1992 | Bahr et al. |
| 5,219,560 A * | 6/1993 | Suzuki et al. ............. 424/63 |
| 5,236,986 A | 8/1993 | Sakuta |
| 5,266,321 A | 11/1993 | Shukuzaki et al. |
| 5,412,004 A | 5/1995 | Tachibana et al. |
| 5,580,921 A | 12/1996 | Stepp et al. |
| 5,599,533 A | 2/1997 | Stepniewski et al. |
| 5,654,362 A | 8/1997 | Schulz, Jr. et al. |
| 5,760,116 A | 6/1998 | Kilgour et al. |
| 5,811,487 A | 9/1998 | Schulz, Jr. et al. |
| 5,849,314 A | 12/1998 | Dobkowski et al. |
| 5,854,336 A | 12/1998 | Divone, Sr. et al. |
| 5,859,069 A | 1/1999 | Yanagida |
| 6,083,901 A * | 7/2000 | Perry et al. ............. 512/2 |
| 6,171,581 B1 * | 1/2001 | Joshi et al. ............. 424/65 |

FOREIGN PATENT DOCUMENTS

| | | |
|---|---|---|
| EP | 0 398 745 A2 | 5/1990 |
| EP | 0 790 055 A1 | 8/1997 |
| EP | 0 848 029 A2 | 12/1997 |
| EP | 0 882 753 A1 | 6/1998 |
| EP | 0 885 932 A2 | 6/1998 |
| EP | 1 057 476 A1 | 5/2000 |
| WO | WO 97/44010 | 11/1997 |
| WO | WO 98/00102 | 1/1998 |
| WO | WO 98/00103 | 1/1998 |
| WO | WO 98/00104 | 1/1998 |
| WO | WO 98/00105 | 1/1998 |
| WO | WO 98/18438 | 5/1998 |

OTHER PUBLICATIONS

English Patent Abstract Corresponding To Japanese Patent No. JP 2172906.
English Patent Abstract Corresponding To Japanese Patent No. JP 1190757.
English Patent Abstract Corresponding To Japanese Patent No. JP 3197413.
English Patent Abstract Corresponding To Japanese Patent No. JP 1207354.
English Patent Abstract Corresponding To Japanese Patent No. JP 61194009.
English Patent Abstract Corresponding To Japanese Patent No. JP 1250305.
International Search Report—mailed May 30, 2001.

\* cited by examiner

Primary Examiner—Robert Dawson
Assistant Examiner—Jeffrey B. Robertson
(74) Attorney, Agent, or Firm—Brooks & Kushman P.C.

(57) ABSTRACT

Organopolysiloxane gels containing gel-bound hydrophillic groups are prepared by reacting a hydrosilylatable unsaturated organopolysiloxane resin, a crosslinker bearing Si—H bound hydrogen, and a hydrosilylatable unsaturated hydrophile, in the presence of an effective amount of a hydrosilylation catalyst, at least a portion of the reaction taking place in the presence of at least 60 weight percent of an oleaginous composition containing at least 50 weight percent low viscosity organopolysiloxane. When sheared, the crosslinked organosiloxane compositions form a stable, preferably incompatible gel which may be used in turn to form a stable emulsion with large amounts of ordinarily incompatible hydrophillic liquids. The emulsions thus formed are suitable for use in a wide variety of cosmetic products.

26 Claims, No Drawings

ORGANOPOLYSILOXANE GELS FOR USE IN COSMETICS

TECHNICAL FIELD

The present invention pertains to organopolysiloxane gels suitable for use in cosmetic applications which can form stable emulsions with hydrophilic liquids such as water and glycols.

BACKGROUND ART

Organopolysiloxanes have been used in numerous cosmetic applications for many years. In some of these applications, for example, organopolysiloxanes such as silicone fluids have been employed, either in their native form as oleaginous carriers for other cosmetic ingredients, or in the form of oil-in-water emulsions. In many of the latter cases, a surfactant is necessary in order to keep the silicone fluid in stable suspension or dispersion. Somewhat more recently, numerous cosmetic formulations have employed creams or pastes which include organopolysiloxane gels containing volatile organosiloxanes.

U.S. Pat. No. 5,654,362 discloses silicone gels prepared by reacting a linear, Si—H functional polysiloxane with an $\alpha,\omega$-diene, for example 1,5-hexadiene, in the presence of a platinum hydrosilylation catalyst and a low molecular weight silicone oil. The reaction is continued until a gel is formed following which the silicone gel may be crumbled into a powder, or by addition of further silicone oil, may form a silicone paste. The products are employed to thicken hydrophobic liquids such as silicone oils to a gel-like consistency. A variety of cosmetic products such as an anti-perspirants, deodorants, skin creams, etc.,are disclosed. The use of expensive and flammable diene hydrocarbons in the preparation is a disadvantage. Moreover, creams formed from solid powders are said not to provide acceptable properties, as indicated by U.S. Pat. No. 4,980,167, wherein such formulations are said to suffer from lack of lubricity. Similar products prepared from $\alpha,\omega$-dienes and polyether-functional siloxanes are disclosed in U.S. Pat. No. 5,136,068. However, preparation of water-in-oil emulsions still required use of a separate emulsifying surfactant.

U.S. Pat. No. 4,987,169 discloses preparation of linear and lightly crosslinked organosiloxanes in the presence of silicone oils to form soft powdery or soft, translucent solid particles. The crosslinked organosiloxanes are preferably prepared employing linear Si—H and vinyl-functional organopolysiloxanes, crosslinked through the aid of a hydrosilylation catalyst. Because of the limited crosslinking of the crosslinked organosiloxanes, the amount of the latter necessary to produce the solid product is high, for example 30 to 50% by weight. The product is thus relatively expensive. The soft powders may be used as thickeners in solubilizing additional silicone oil to form greasy compositions stated to be useful in cosmetics and lubricants. The deficiencies of the '169 patent are attested to in U.S. Pat. No. 5,760,116, which discloses products prepared in two stages, in a first step, preparing a highly crosslinked gel from an Si—H functional organopolysiloxane resin in the presence of a minor amount of low viscosity organopolysiloxane, and in a second step, adding further organopolysiloxane oil by means of a homogenizer into the gel by means of a homogenizer to produce a clear, highly viscous liquid. The disadvantage of two stage production is clear.

U.S. Pat. No. 5,859,069 discloses a gelatinous external skin treatment composition prepared from an organopolysiloxane elastomer powder having spherical particles with an average particle size of 1.0 to 15.0 $\mu$m, a silicone oil, and a polyether-modified silicone. The '069 patent indicates that prior formulations employing silicone resins are unsuitable for such uses, as they leave a filmy feeling on the skin. The polyether-modified, resin-free (linear) silicone is disclosed as being absolutely necessary; and if amounts of less than 1.0% by weight are used, gelation becomes insufficient and the composition becomes unsuitable for use in cosmetics. Gelatinous external skin treatment compositions containing the spherical powder, 5–75% by weight of silicone oil, and 1–20% by weight of polyether-modified silicone are disclosed. Preparation of spherical elastomer particles is not straightforward, and creams containing solid powders have been viewed as undesirable, as previously discussed.

Polyether-functionalized silicone surfactants are disclosed in U.S. Pat. Nos. 5,412,004 and 5,236,986. In each case, a polyether-functional linear Si—H containing organopolysiloxane is reacted with an $\alpha,\omega$-divinyl organopolysiloxane. A further series of compounds are prepared by cross-linking employing an $\alpha,\omega$-bis(unsaturated) polyoxyalkylene polyether instead of the $\alpha,\omega$-divinylsiloxane. However, gels are not formed, and incorporation of silicone oil into the compositions must be performed using high shear kneading. The products contain a high weight percentage of polyether moieties (ca 15% in the examples). The synthesis must necessarily take place in several steps. The additional step of kneading with silicone oil is disadvantageous. Moreover, the $\alpha,\omega$-bis(unsaturated) polyethers are expensive to prepare.

U.S. Pat. No. 5,811,487 describes low molecular weight siloxane fluids thickened with silicone elastomers prepared by reaction of Si—H functional siloxanes and an $\alpha,\omega$-unsaturated diene hydrocarbon, the Si—H siloxane first having been partially reacted with a monoalkenyl functionalized polyether to provide polyether functionality. The necessity of employing $\alpha,\omega$-dienes is disadvantageous, as previously discussed.

U.S. Pat. No. 5,854,336 discloses a process for preparing cosmetic products which involves feeding a silicone elastomer composition consisting of a silicone rubber and a carrier fluid into a reactor, mixing the composition in the reactor, delivering the composition from the reactor to a high pressure pump, and from there into a device for reducing the particles of rubber into smaller sizes. The device for reducing particle size is preferably a high pressure feed homogenizer, most preferably a sonolator. Use of high pressure pumps and devices such as sonolators increase the expense of the product. Stable emulsions and creams containing water and glycols either cannot be prepared, or are difficult to prepare, due to the incompatibility of the hydrophobic silicone and hydrophilic water/glycols.

EP 0 790 055 A1 discloses compositions containing a partially reticulated elastomeric organopolysiloxane and a fatty component such as a triglyceride for use in skin care or make-up formulas. What is meant by "partially reticulated" is not defined in the specification, which refers to U.S. Pat. No. 5,266,321 for its description of suitable organopolysiloxanes.

Examples of cosmetic formulations employing silicone gels are also disclosed in International PCT Applications WO97/44010; WO98/18438; WO98/00105; WO98/00104; WO98/00103; WO98/00102, and like patents. It can be clearly seen from such patents that the range of formulations includes anti-perspirants, both liquid and solid, facial creams, moisturizers, and other products. It should also be apparent from a review of these references that there are considerable differences between the variety of organosilicone gels. In particular, some of these gels provide an unacceptable oily feeling when such is not desired. Other gels are more difficult to produce, and unnecessarily increase the cost of formulation. It would be desirable to be able to produce gels in a simple fashion from well-recognized readily available, and essentially non-toxic ingredients, to produce a product which avoids the stringiness of other gels, which can be emulsified without the use of extremely high pressure devices such as sonolators and the like, and without extensive high shear kneading, and which may produce cosmetic products devoid of oiliness or filmy sensation when applied to the skin.

SUMMARY OF THE INVENTION

It has now been unexpectedly discovered that organopolysiloxane gels containing a low viscosity and preferably volatile silicone oil, which can be emulsified with water and other hydrophilic liquids to form stable emulsions, may be easily prepared by the hydrosilylation reaction of an unsaturated MQ resin and an unsaturated hydrophile with an Si—H functional polyorganosiloxane in the presence of the low viscosity fluid and an effective amount of platinum hydrosilylation catalyst. It has also been discovered that addition of relatively small amounts of hydrosilylation catalyst poisons such as organosulphur compounds, particularly mercaptoalkyl-functional organopolysiloxanes, produces compositions which retain their stability over longer periods of time than when the organosulphur compounds are not employed. The resulting gels are ideally non-stringy gels which can be prepared in but one process step, and which may be easily homogenized to form a stable cream or paste without the use of high pressure or other complex mixing arrangements. The gels can be emulsified with considerable quantities of water, or alcohols or glycols, for example glycerine, ethylene glycol, and propylene glycol.

DESCRIPTION OF THE PREFERRED EMBODIMENTS

The organopolysiloxane gels of the subject invention contain a low viscosity and preferably volatile silicone oil, intimately associated with a gel matrix produced by the cross-linking of a vinyl functional MQ resin with an Si—H functional organopolysiloxane which contains Si—H functionality distributed along its backbone rather than exclusively at the termini, in the presence of an effective amount of an unsaturated hydrophile, the latter preferably employed in the amount of from 0.2 to 5 weight percent.

The low viscosity and preferably volatile organopolysiloxane may be a low molecular weight oligomeric polydialkylsiloxane, or a cyclic siloxane. Most preferably, the low viscosity organopolysiloxane is an oligomeric polydimethylsiloxane or a cyclic polydimethylsiloxane. Other alkyl, aryl, alkaryl, and aralkyl groups are also acceptable, of course, for example, phenyl groups, benzyl groups, $C_1$–$C_{18}$ alkyl groups, and the like. However, because of cost considerations and the ease of formulation, organopolysiloxanes with methyl groups attached to the silicon atoms are highly preferred. Most preferably, the organopolysiloxanes are linear trimethylsilyl terminated polydime thylsiloxanes having on average from 2 to 50 silicon atoms in the organopolysiloxane backbone inclusive of the trimethylsilyl end groups. If volatility is desired, the number of silicon atoms should be greatly restricted, for example, to below 10, and preferably below 6. However, if relatively low viscosity but non-volatile fluids can be tolerated , extensions of the organopolysiloxane backbone to higher numbers of silicon atoms, for example, to 50 or 500 silicon atoms is possible. These non-volatile fluids should have viscosities greater than about 10 cSt, and up to about 2000 cSt. The organopolysiloxanes may also be slightly cross-linked, as long as the cross-linking does not overly increase the viscosity. Viscosity is preferably below 100 cSt, more preferably below 10 cSt, and most preferably, in the case of volatile organopolysiloxanes, less than 5 cSt.

Preferably, the organopolysiloxanes are volatile organopolysiloxanes. As indicated previously, volatility can be achieved in linear organopolysiloxanes by selection of oligomeric organopolysiloxanes with at most about 6 to 10 silicon atoms in the organopolysiloxane backbone. Preferably, however, cyclic organopolysiloxanes having from 3 to 6 silicon atoms are utilized, for example, octamethylcyclotetrasiloxane, decamethylcyclopentasiloxane, dodecamethylcyclohexasiloxane, and the like. As with the linear organopolysiloxanes, groups other than methyl groups may be present, for example, $C_1$–$C_{18}$ alkyl groups, preferably $C_{1-4}$ alkyl groups, aryl groups, and the like. In addition, and also as is the case for the linear polysiloxanes, functional groups which do not interfere with the stability of the organopolysiloxane gels or with the ability to use these in cosmetic formulations may be tolerated. In particular, examples include hydroxyl (silanol) groups, alkoxy groups, for example, those which are relatively hydrolytically stable, and the like. Compounds containing reactive groups such as acetoxy groups, methoxy groups, ethoxy groups and the like, should generally be avoided unless they are retained for some special purpose in the cosmetic formulations. It is not desired to include any halo-functional compounds in the organopolysiloxane gels. Please note in this respect that minor amounts of such groups are sometimes unavoidable in organosiloxane resins due to their method of preparation.

Up to 50 percent by weight of the low molecular weight organopolysiloxane component may be replaced by one or more oleaginous substances. Thus, in the claims, the term "oleaginous composition" is used to describe the oily, hydrophobic component containing minimally 50 weight percent organopolysiloxane which is added during preparation of the gel. This composition does not include any additional oils which may be later added following preparation of the gel, by dissolution, emulsification, or dispersion prior to, concurrently with, or following emulsification of the hydrophilic liquid(s), into the gel to form a hydrophilic liquid-containing emulsion.

Suitable oily substances include vitamin oils such as vitamins A or E or related compounds such as α-tocopheryl acetate; fatty oils, including ω-3 and ω-6 polyunsaturated fatty acids and their esters, retinol, retinoic acid, esters of the latter retin compounds; vegetable oils such as peanut, olive, palm, cannola, sunflower, and the like; mineral oils; flavoring or "essential" or "aromatic oils" such as the various terpenes both natural and synthetic, patchouli, myrrh, frankincense, lavender, vanillin, sandalwood, eucalyptus, camphor, menthol, and the like, or oily substances such as benzaldehyde, cinnamaldehyde, and the like; and natural and synthetic oils or oil-soluble solids such as various mono-, di- and triglycerides, polyoxyalkylated vegetable oils, lanolin, lecithin, and the like. More preferably, the oleaginous composition contains 70% or more low molecular weight, preferably volatile organopolysiloxanes, more preferably 80% or more, and most preferably 90% or more. Oleophilic solvents, particularly low odor paraffinic solvents which are pharmaceutically acceptable and have boiling points below 200° C., preferably in the range of 60° C. to 150° C., may also be part of the oleaginous component in amounts of less than 30% by weight based on the total weight of this component.

A necessary component of the reaction mixture used to prepare the organopolysiloxane gel is a vinyl functional MQ resin or similar, highly crosslinked resin containing M, D, Q, and/or T moieties. Such resins are by now well-known in the art. In the organopolysiloxane art, the term "resin" is not applied to polymers in general, but is restricted for the use in describing relatively highly cross-linked and often high molecular weight products produced by the reaction of silanes which are capable of forming three-dimensional networks. The term M refers to monofunctional units while the term Q refers to tetrafunctional units. In other words, an MQ resin contains predominantly M units wherein silicon is attached to only one oxygen in the cross-linked molecules, and $SiO_{4/2}$ Q units wherein each silicon atom is attached to four other oxygen atoms, resulting in a high level of cross-linking. In some MQ resins, small amounts of difunctional $R_2SiO_{2/2}$ and trifunctional $RSiO_{3/2}$ (D and T units, respectfully), are also present. MQ resins are frequently produced by the hydrolysis of silanes such as tetraethoxysilane, vinyldimethylethoxysilane and trimethylethoxysilane. The resulting MQ resin frequently retains some residual alkoxy functionality as a result of the method of its preparation, and will occasionally include other functionalities such as silanol functionality as well. A preferred MQ resin is MQ resin 804, available from Wacker Silicones Corporation, Adrian, Mich., which contains approximately 1.2 to 1.8 eight percent vinyl functionality. MQ resins having unsaturation other than vinyl, including vinyloxy, allyl, allyloxy, propenyl, etc., are less commonly available, but may be used also. The various unsaturated resins may be used alone or in admixture with other unsaturated resins. Minor amounts of unsaturated non-resinous organopolysiloxanes may be used as well, provided a stable gel can be obtained. The term "resin" used herein in its customary meaning, i.e. a highly three dimensionally crosslinked polymer containing a majority of M, T, and Q units.

The Si—H functional organopolysiloxane cross-linking agent is a necessary part of the present gel formulation. While Si—H-terminated organopolysiloxanes may be used as crosslinkers, past experience indicates that gels may tend to have a stringy appearance. Allyl polyethers will react with the terminal Si—H groups thus acting like end-caps and inhibiting the crosslinking reaction. Theoretically, an excess of Si—H terminated silicones could form a gel. However a stringy gel without a high degree of three dimensional crosslinking would be expected. Preferably the crosslinker must comprise, in substantial part, an Si—H functional organopolysiloxane which contains Si—H functional units along its polymer backbone. The Si—H functional organopolysiloxane may or may not, in addition to these Si—H functional units, also include terminal Si—H units. A preferred crosslinker is EL Crosslinker 525, a poly (methylhydrogen)-dimethylsiloxane containing approximately 0.54 weight percent silicon-bonded hydrogen atoms. The crosslinkers preferably contain in excess of 5 Si—H bound hydrogens per molecule, more preferably 10 or more, and most preferably 20 or more. In addition to these highly Si—H functional crosslinkers, minor amounts, i.e., 50% or less or a weight basis, of lesser functional crosslinkers may be used.

The ratio of moles of unsaturation in the resin to moles of Si—H is preferably in the range of 0.4 to 2.0, more preferably 0.5 to 1.5, and most preferably 0.6 to 1.2. Ratios of 1.10 to 1.20 have proven quite satisfactory when MQ resins are employed.

An unsaturated hydrophile susceptible to hydrosilylation is also required. The hydrophile is responsible for supplying compatibility with water and other relatively hydrophilic substances such as alcohols, glycols, and the like. The unsaturation is preferably allylic, but may also be vinyl or in general, alkenyl. Examples of hydrosilylatable unsaturated moieties include, allyl, vinyl, (meth)acryloyl, allyloxy, vinyloxy, maleate, fumarate, and the like.

The hydrophilic function is supplied by a hydrophilic polyether group, or by polar groups such as hydroxyl groups, amide groups, carboxyl groups and their salts, etc. Most preferably, the hydrophilic groups are non-ionic hydrophiles such as polyoxyalkylene groups, polyglycol moieties, oligosaccharides, and the like. Polyoxyethylene groups are the preferred hydrophiles, for example those containing 3 to 50 oxyalkylene groups, particularly those containing four or more, preferably 4–50, and more preferably 5 to 20 repeating oxyethylene and/or oxypropylene groups, as well as those containing low numbers of oxypropylene groups may also be suitable. Thus, the preferred hydrophiles correspond to the formula

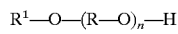

where $R^1$ is an unsaturated hydrocarbon, R is an alkylene group, preferably methylene, ethylene, methylethylene, 1,3-propylene or tetramethylene, and n is from 3 to about 20. Most preferred unsaturated hydrophiles correspond to the formula

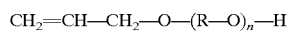

where R is defined as before and n is 4–50, preferably 5–20, and more preferably 5–12. The distribution of alkylene groups when different alkylene moieties are present may be random, block, block-random, or any other distribution employed in polyether surfactants. Non-ionic hydrophiles are most preferred.

Preferred hydrophiles are prepared by oxyalkylating allyl alcohol in the presence of basic catalysts to form allyloxy-terminated, ω-hydroxy polyether monols. Allyloxy-functional polyoxyethylene monols are commercially available from Rhodia Inc. as Rhodasurf AAE-10 and from the Dow Chemical Company as AE-400. Both products are nominal five to ten mole oxyethylated allyl alcohol adducts containing a range of oligomers. Also suitable as hydrophiles are oxyethylated unsaturated diols such as oxyethylated 1,4-butenediol and 1,4-butynediol, and oxyethylated unsaturated carboxylic acids, particularly ω-alkenoic acids, or unsaturated diacids such as fumaric acid, maleic acid, and the like. Hydrophiles with carboxylate ester end groups or alkyl ether end groups are also useful, particularly esters of lower $C_{2-4}$ alkanoic acids and ethers of lower $C_{1-4}$ alkanols. Acetates and methoxy and ethoxy ethers are some preferred carboxylate and ether terminal groups. The end groups may also be carboxylic acid groups, sulfonate groups, phosphanate groups, or their esters or salts. The same modifications may be made to other unsaturated hydrophiles.

Also suitable are alkenyl-functionalized polyhydroxy substances such as polyglycerols and oligosaccharides. Polyglycerol, for example, may be functionalized with allyl groups by reaction with allyl chloride to form the polyglycerol allyloxy ether, or with propenoic acid, propenoyl chloride, maleic acid, maleic anhydride, or maleic acid chloride to form the corresponding carboxylic acid ester(s). Syntheses for such compounds may be found in the literature. Functionalization may also be accomplished by reaction with unsaturated isocyanates such as 1-isocyanato-1,1- dimethyl-4-isopropenylbenzene (TMI) or isocyanatoethylmethacrylate. Polyglycerols and oligosaccharides and similar hydrophiles may be modified to contain methoxy, ethoxy, carboxymethyl, or other modifying groups.

The amount of hydrophile must be sufficient to form a stable emulsion having the desired water/glycol content. For example, in general, less hydrophile content will be required when a 20% aqueous (water content) emulsion is to be formed than when a 30% aqueous emulsion is to be formed. The amount will also depend upon the HLB of the hydrophile, and the number and nature of polar groups. For example, relatively larger quantities of low HLB oxyethylates such as the three mole oxyethylate of allyl alcohol will ordinarily be necessary as compared to the analogous 10 mole oxyethylate which has a much higher HLB. Hydrophiles with large numbers of hydroxyl groups will ordinarily be required in lesser amounts than non-functional hydrophiles or hydrophiles with but a single polar functionality. Lesser amounts of hydrophiles or use of hydrophiles with lower HLB may be dictated when less polar liquids such as ethylene glycol, propylene glycol, 1,3-propanediol, or glycerine are to be emulsified into the gel. Mixtures of hydrophiles may be advantageous.

While the amount of hydrophile is dependent upon the amount and nature of the substance to be incorporated into the emulsion (water, propylene glycol, etc.), the amount of hydrophile is also tied to the amount and nature of the low viscosity organopolysiloxane which is also part of the gel. In general, large amounts of very hydrophilic (i.e., high HLB) or polar (i.e., polyhydroxyl) groups destabilize the organopolysiloxane gel. The gel may become stringy, grainy, may solidify into a soft powder, or may itself separate. While stringy or grainy gels may at times be acceptable, soft or crumbly powders or solids or gels which exhibit separation are not. Thus, the amount of hydrophile is often a compromise between the amount which can be tolerated in the organopolysiloxane gel initially formed, and the amount required to form a stable emulsion.

The effective amount of any given hydrophile is easily determined by preparation of a series of organopolysiloxane gels containing varying amounts of the hydrophile under consideration. A stable gel indicates that the amount of hydrophile is sufficient for this purpose (gel formation), and testing for emulsion stability is then performed. If a stable emulsion containing the desired amount of polar solvent, i.e., 20 weight percent water, or 15 weight percent water and 10 weight percent propylene glycol, can be prepared, then the amount of hydrophile is an "effective compatibilizing amount" as herein defined. Note that both a stable organopolysiloxane gel as well as a stable emulsion must result. Organopolysiloxane gels which may be described by such terms as pasty, stringy, grainy, are suitable, provided that they are stable to separation and are capable of forming a smooth stable, emulsion with the desired quantity of polar solvent. However, it is most preferred that the gels themselves be smooth gels. Reaction of Si—H terminated polysiloxanes and unsaturated organopolysiloxane in the absence of unsaturated hydrophiles has been demonstrated in the past to produce only stringy gels.

It has been found in practice, that when employing 10 mole oxyethylated allyl alcohol hydrophiles, a preferred hydrophile, amounts of less than 0.3 weight percent hydrophile based on the weight of the organopolysiloxane gel are generally not suitable for forming stable emulsions from greater than 10–15 weight percent water. Amounts of about 0.6 weight percent have proven highly suitable for preparing emulsions containing up to about 40–50 weight percent of water, or 30 weight percent propylene glycol. Most preferably, the minimum amount of unsaturated hydrophile is about 0.1 weight percent based on the total weight of the gel. Amounts of about 2 weight percent or more of this hydrophile have been found to cause instability of the organopolysiloxane gel. With respect to the gel itself, a gel is considered within the scope of the intention if it can form a stable emulsion with a greater amount of hydrophilic liquid than a similar gel prepared from a composition containing no unsaturated hydrophile.

Use of two hydrophobes of differing HLB may be useful in preparing gels which are stable and yet contain larger quantities of hydrophile. For example, polyoxypropylated allyl alcohol is much less hydrophilic than its polyoxyethylated analog. However, polyoxypropylene groups do not become hydrophobic until their molecular weight reaches the neighborhood of 500 Daltons (Da). The use of less hydrophilic polyoxypropylates of allyl alcohol together with a more hydrophilic hydrophile such as an allyloxy polyglycerol, allyloxy oligosaccharide, or polyoxyethylated allyl alcohol may provide both high gel stability as well as high emulsion stability. In a similar vein, broad or bimodal distributions of polyoxyalkylated allyl alcohol oligomers may provide similar benefits.

A hydrosilylation catalyst is also required. Suitable hydrosilylation catalysts are well-known, and widely available from numerous sources. Preferred hydrosilylation catalysts are platinum compounds such as those disclosed in U.S. Pat. Nos. 3,159,601; 3,159,662; 3,220,972; 3,715,334; 3,775,452; and 3,814,730, and German published application DE 195 36176 A1, preferably supplied in a solvent suitable for use in cosmetic formulations, such as propanediol. Most referred is Catalyst OL, a divinyl-terminated polydimethylsiloxane platinum complex diluted with polydimethylsiloxane, and available from Wacker Silicones, Adrian, Mich. Other solvents may be used as well for dilution of the catalyst, provided that they are cosmetically acceptable, or can be removed from the gel, for example, by exposure to low pressures or stripping.

The amounts of low viscosity organopolysiloxane fluid, unsaturated resin, and crosslinker are not critical. However, these necessary components must be present in such quantities that a stable gel is obtainable which will not separate upon standing. If too little unsaturated resin or too little crosslinker is used, the composition will frequently remain liquid instead of gelling. If too much crosslinker or resin is employed, a solid or crumbly gel or powder will be obtained. The actual amounts of ingredients can be determined by simple experimentation. Preferred compositions contain from about 60% to about 90% oleaginous composition, from about 5% to about 25% unsaturated resin, and from about 1% to about 8% Si—H functional crosslinker. More preferably, the compositions contain from 60 to 85% by weight oleaginous composition, 10 to 20% unsaturated resin, and 1 to 5% crosslinker. Compositions containing 75–80% organopolysiloxane, 15–20% vinyl-functional resin, and 2–3% crosslinker have proven exceptionally useful. Compositions containing 10 to 30% of unsaturated MQ resin, 1 to 5% of Si—H functional crosslinker, 0.1 to 5% of unsaturated hydrophile, and 88% to 60% of oleaginous component are also useful. Such compositions may, for example, contain an MQ resin having a vinyl unsaturation content of 1.0 to 2.0% by weight present in an amount of 15% to 20% by weight; an Si—H polyorganosiloxane crosslinker comprising dimethylsiloxy and hydrogenmethylsiloxy repeating units with an Si—H bound hydrogen content of 0.1 to 1.0 weight percent, present in an amount of from 1 to 3 weight percent by weight; as a hydrophile, an oxyethylated allyl alcohol present in an amount of 0.1 to 2 weight percent; and an oleaginous substance comprising minimally 80% by weight low viscosity organopolysiloxane and present in an amount of 50% to about 84% based on the weight of the gel. These percentages are percentages by weight based on the total weight of the gel, and are based on an MQ resin having about 1.2 to 1.8 weight percent vinyl functionality and a crosslinker containing about 0.5 weight percent Si—H bound hydrogen distributed predominately along the polysiloxane chain. Resins and crosslinkers with higher functionalities may be used in lesser amounts and vice versa. The functionality must not be too high, or a solid, too highly crosslinked product may be obtained. The amount, functionality, and molecular weight of the MQ resin and Si—H crosslinker may be easily determined by one skilled in the art.

The preparation of the gel is readily accomplished. In general, all of the ingredients except the catalyst are added and stirred slowly until a homogenous mixture is obtained, following which the catalyst is added with continual stirring. The hydrophile is preferably added last before the catalyst. The composition can be left at room temperature until a gel is formed, or can be heated. Preferably, the composition is heated to a temperature between 50° C. and 100° C., more preferably between 60° C. and 90° C. until the mixture solidifies or gels. The 90 to 100° C. range is preferred with Pt/propandiol, but temperatures of approximately 60° C. are preferred with Catalyst OL. Gelation typically takes place within several minutes to five hours, preferably within a maximum of about three hours, and typically in about a half hour. The gel is then homogenized to a smooth consistency using standard high shear mixing techniques such as the use of an Ultra-Turax™ mixer or the like. High pressure mixing and recirculated mixing techniques are not necessary, although they may be practiced if desired.

Following homogenization of the gel to a creamy consistency, numerous cosmetic ingredients can be added, such as perfumes, emollients, lanolin, oils, pigments, U.V. absorbers, dyes, etc. Thickeners such as pyrogenic silica and other ingredients may also be added at this point to increase the viscosity of the cream to form paste-like products. The hydrophilic liquid may be added prior to or after the addition of these other ingredients to form the emulsions of the subject invention.

The number and type of cosmetic ingredients which may be added is not overly critical, and can be easily selected by one skilled in the art. In the application herein the term "cosmetically acceptable ingredients" includes all ingredients which can be added by a cosmetic formulator which are cosmetically acceptable for use on the skin. Many such ingredients are listed in standard references, for example INTERNATIONAL COSMETIC INGREDIENT DICTIONARY AND HANDBOOK,© 1997, Cosmetic, Toiletry and Fragrance Assoc., Washington, D.C.

Suitable fillers include all those commonly employed. All or part of the filler may be added prior to gelation; however, it is highly preferred to form the gel first and to add filler with stirring to obtain a homogenous-appearing mixture. Examples of fillers include fumed or pyrogenic silica, precipitated silica, other silaceous fillers, and in particular silaceous fillers having a BET surface area greater then 50 $m^2/g$; metal silicates, particularly those containing metals of Groups 1 and 2 of the periodic table; diatomaceous earth; precipitated calcium carbonate; fuller's earth; clay minerals, e.g., smectite clays, including bentonite, wollastonite, etc.; kieselguhr; chalk; transparent iron oxides, and the like. Those fillers which are colored can be simultaneously used as pigments herein. Fillers may preferably be employed in amounts of 0.05 to 40 weight percent, more preferably 0.1 to 25 weight percent, and most preferably 0.5 to 10 weight percent. Fillers of high surface area are generally used in lesser amounts than low surface area fillers, due to the viscosity-increasing effect of the former.

As indicated previously, two types of stability are referred to herein: gel stability and emulsion stability. Both are somewhat similarly assessed. Gel quality may be qualitatively assessed by observation of the texture of the gel after high shear mixing. Most preferably, the gel thus produced is a smooth, creamy, non-stringy lotion, cream, or paste. While such uniform products are preferable, products which are somewhat stringy, or grainy (e.g., applesauce-like in texture), while less desirable, may also be suitable provided they are stable and form stable emulsions as well.

Stability of the gel is preferably assessed visually after long term storage, however a quicker but qualitative assessment is by centrifugation. A lotion, cream, or paste produced by shearing the gel, which is stable against more than minor separation after two months storage at room temperature, is considered stable. A minor amount of separation is observed where a small amount of liquid separates from the emulsion. Separated liquid can generally be found at the bottom or the top of the lotion, cream, or paste depending upon the relative densities of the components. Preferably, no phase separation is visible for two months, and most preferably for a year or more.

The lotion, cream, or paste gel product may also be centrifuged in a standard laboratory centrifuge using 50 g sample cups. A rotational speed of 2000 rpm is suitable. Separation may be recorded in ml. Preferably, the amount of separation after one hour is less than 1 ml, more preferably less than 0.5 ml, and yet more preferably less than 0.1 ml. No separation is most preferred. However, it must be remembered that centrifugation is a somewhat extreme test, and compositions with moderate separation, i.e., 1–3 ml, may still be suitable if separation does not occur at room temperature in non-centrifuged samples over a long period of time. Centrifugation is a rapid means of assessment which is not always definitive.

A hydrophilic liquid-containing emulsion is stable following preparation if the emulsion has a smooth consistency and does not display phase separation under room temperature storage. Unlike the gel, emulsions which are grainy or stringy are not suitable in the present invention. Emulsions may be clear, translucent, opaque, or pearlescent, but should be smooth and uniform. The centrifuge test may be used to screen emulsions, as with the gels. However, as with the gels, long term storage stability rather than passing any given centrifuge stability test, is the object.

The gels produced herein generally and preferably have a % polysiloxane solids of from 15 to 25, a flash point of 122° F. (50° C.) or higher, a specific gravity just under 1.0, for example between 0.92 and 0.98, a Brookfield viscosity (spindle 6, 5 rpm or $8.3 \times 10^{-2} s^{-1}$) of 80,000 to 150,000 cPs, preferably 100,000 to 120,000 cPs, and a texture hardness at 20 mm (g) of 15–30, preferably 20. The gels preferably exhibit a water "solubility" (stable emulsion) of up to 50% by weight based on total emulsion weight, preferably in the range of 20–40%, and a propylene glycol "solubility"

(stability) of more than 10%, preferably in the range of 20% to 40%. These figures refer to the amount of hydrophilic liquid, on a weight/weight basis, which can be added and yet form a stable hydrophilic liquid-containing emulsion. Thus, the term "solubility" does not mean actual solubility in the traditional sense in this paragraph.

The creamy gels of the subject invention may be used in all cosmetic formulations where silicone emulsions and other products have been used in the past, including, without limitation, skin care products such as antiperspirants, deodorants, sun care, after sun care, moisturizers, creams and lotions; color cosmetic products, such as facial powder, eye powder, eye shadow, liquid foundation, liquid-to-powder foundations, and lipsticks; and hair care products such as hair conditioners, volume enhancers, and the like.

Having generally described this invention, a further understanding can be obtained by reference to certain specific examples which are provided herein for purposes of illustration only and are not intended to be limiting unless otherwise specified.

The overall procedure followed for gel preparation is as follows: In general, a 500 ml flask equipped with desiccator-capped condenser, heating mantle, metal stirrer with bearing, and temperature controller, is charged with unsaturated MQ resin, Si—H crosslinker, and oleaginous composition, and homogenized by stirring. In general, a true solution of these ingredients will be formed, although this is not necessary. The unsaturated hydrophile is then added slowly with stirring, lump formation being avoided if at all possible. While stirring at 5 s$^{-1}$, the catalyst solution is added, and the mixture heated until gel formation is observed. Heating is preferably limited so as to keep the temperature below 100° C. It most cases, the temperature ranged from ambient to about 90° C. over a period of about 25 minutes. Following gelation, heating may be discontinued, but is preferably continued for about 30 minutes to achieve higher completion of the crosslinking reaction. The product is cooled to 40° C. and inhibitor (if used) added. The product is then homogenized to a creamy gel using an Ultra Turrax® mixer. Appropriate physical measurements are taken as desired, and stability is assessed. Larger batches, of course, require a larger reaction vessel. In the Examples and tables, all percentages are in weight percent unless indicated otherwise.

EXAMPLES 1–8 AND C1–C2 GEL PREPARATION

A number of organopolysiloxane gels were prepared in accordance with the procedure outlined previously, employing decamethylcyclopentasiloxane, a volatile cyclic siloxane, as the low viscosity oleaginous fluid. The catalyst employed in Comparative Example C1 and Examples 2–5 is a 2.94 weight percent solution of hexachloroplatinic acid in 1,2-propanediol. The catalyst employed in Comparative Example C2 and Examples 6–8 is Catalyst OL, a platinum catalyst available from Wacker Silicones, Adrian, Mich. The polyglycol used in Examples 1–5 is Dow AE-400, while Examples C2 (comparative) and 6–8 employed Rhodasurf™ AE-10.

| Example | C1 | 1 | 2 | 3 | 4 | 5 | C2 | 6 | 7 | 8 |
|---|---|---|---|---|---|---|---|---|---|---|
| D5 cyclosiloxane % | 79.6 | 79.4 | 78 | 79.0 | 79.0 | 79.0 | 79.4 | 79.0 | 79.0 | 79.3 |
| MQ resin 804% | 17.45 | 17.41 | 17.41 | 17.73 | 17.69 | 17.45 | 17.73 | 17.96 | 17.96 | 17.96 |
| EL Crosslinker 25% | 2.50 | 2.49 | 2.49 | 2.22 | 2.21 | 2.49 | 2.22 | 2.00 | 2.00 | 2.00 |
| polyoxyethylated allyl alcohol hydrophile % | — | 0.617 | 2 | 0.617 | 0.617 | 0.617 | 0.617 | 0.617 | 0.617 | 0.30 |
| hydrosilylation catalyst % | 0.0526 | 0.100 | 0.100 | 0.0526 | 0.100 | 0.0526 | 0.0500 | 0.0500 | 0.0500 | 0.0500 |
| inhibitor % | 0.40 | — | — | 0.40 | 0.40 | 0.40 | — | 0.40 | 0.40 | 0.40 |
| batch size (g) | 400 | 400 | 400 | 800 | 400 | 400 | 400 | 400 | 3700 | 3700 |
| initial % H | 0.0135 | 0.0134 | 0.0134 | 0.0120 | 0.0119 | 0.0134 | 0.0120 | 0.0108 | 0.0108 | 0.0108 |
| mol PEG Vi/mol H | — | 0.10 | 0.32 | 0.11 | 0.11 | 0.10 | 0.11 | 0.10 | 0.10 | 0.05 |
| mol resin Vi/mol H | 0.59 | 0.59 | 0.59 | 0.67 | 0.67 | 0.59 | 0.99 | 1.12 | 1.12 | 1.12 |
| viscosity (cP) | 92000 | 120000 | 47200 | 59200 | 20000 | 128000 | 132000 | 104000 | 95200 | 118000 |
| characteristics | creamy gel | creamy gel | creamy gel wet | creamy gel | pourable | grainy | grainy | creamy gel | creamy gel | creamy gel |
| % H (final) | 0.0063 | 0.0036 | 0.0019 | 0.0039 | 0.0043 | 0.0043 | 0.0025 | 0.0035 | 0.0035 | 0.0029 |
| H final/H initial | 0.47 | 0.27 | 0.14 | 0.33 | 0.36 | 0.32 | 0.21 | 0.32 | 0.32 | 0.27 |
| turbidity (NTU) | 48 | 200 | 100 | 390 | 200 | 190 | 180 | 290 | 240 | |
| flash point (° C.) | 76 | 63 | 50 | 58 | 53 | 70 | 56 | 74 | 62 | 59 |
| specific gravity | — | 0.94 | — | 0.95 | — | — | — | — | — | — |
| texture 20 mm (g) | 18 | — | — | 14.4 | 20.4 | 43 | 42 | 22 | 20, 19 | 23 |

Examples 1–8 all produced suitable gels, exhibiting acceptable stability in all cases. The gels of Examples 2, 4, and 5 were not optimally creamy, but showed no evidence of separation. Examples 1, 3, 6, 7, and 8 all produced uniform, creamy gels. Examples 7 and 8 were produced in larger batch sizes following the same procedure, to partially assess commercial producibility which would be performed at yet higher volume.

Comparative Example C1 produced a creamy gel. However, this gel contained no unsaturated hydrophile component. As a result, while suitable for some uses, it cannot be used to form a stable emulsion with any significant amount of water or other hydrophilic liquid without the addition of emulsifying surfactants which are undesirable in many cosmetic formulations. Comparative Example C2 illustrates a product which is somewhat over crosslinked.

Some of the gels were tested to demonstrate that the amount of hydrophile incorporated by hydrosilylation, while being insufficient to destroy the stability of the organopolysiloxane gel, is sufficient to allow incorporation of significant amounts of hydrophilic liquids to form stable emulsions. It should be noted that the gels of the subject invention are all capable of forming stable emulsions with greater quantities of hydrophillic liquids than otherwise similar gels prepared without the unsaturated hydrophile component. It is preferred that the gels be suitable for use with minimally 5% by weight hydrophilic liquid, more preferably minimally 10% by weight, and yet more preferably minimally 15% by weight.

Water-Containing Emulsion Examples 9–13 and Comparative Example C4

The organopolysiloxane gel of Example 7 was employed to form hydrophilic liquid-containing emulsions. To a quantity of gel was added sufficient water to form 5% to 50% water content emulsions. The water was slowly sheared into the gel using an Ultra-Turrax® mixer at ambient temperature. The compositions and results are presented in Table 2.

TABLE 2

| Example | 9 | 10 | 11 | 12 | 13 | C14 |
|---|---|---|---|---|---|---|
| Organopolysiloxane gel (g) | 380 | 360 | 320 | 280 | 240 | 200 |
| water (g) | 20 | 40 | 80 | 120 | 160 | 200 |
| weight percent water | 5% | 10% | 20% | 30% | 40% | 50% |
| Emulsion Formed? | Yes | Yes | Yes | Yes | Yes | No |
| Brookfield Viscosity cPs (spindle 6, 5 rpm) | 160,000 | 184,000 | 192,000 | 204,000 | 208,00 | — |
| Comments | Stable, no separation | Stable, no separation | Stable, no separation | Stable, no separation | Stable, slight[1] separation | — |

[1]A few drops of water were observed to separate after 16 hours.

Of the subject invention emulsions, only Example 13 exhibit any separation, and that separation is slight and acceptable for most uses though not desirable. Even at this high level of water incorporation, fine tuning of hydrophile type and/or amount should be able to produce an organopolysiloxane gel which can produce a more stable emulsion. Comparative Example C14 would not emulsify at 50% water. While the gel used in this Comparative Example is a gel of the subject invention, the water-containing composition, forming no stable emulsion, is not.

Propylene Glycol-Containing Examples 15–19

In similar fashion to the preceding Examples, emulsions of propylene glycol and both propylene glycol and water are prepared. The results are as follows:

TABLE 3

| Example | 15 | 16 | C17 | C18 | 19 |
|---|---|---|---|---|---|
| Organopolysiloxane gel | 360 | 210 | 280 | 200 | 360 |
| Propylene glycol (g) | 40 | 90 | 120 | 200 | 20 |
| Weight Percent Propylene glycol | 10% | 30% | 40% | 50% | 5% |
| Water (g) | — | — | — | — | 20 |
| Water (%) | — | — | — | — | 5% |
| Emulsion formed | yes | yes | yes[1] | no | yes |
| Viscosity @ cPs (spindle 6, 5 rpm) | 80,000 | 86,000 | — | — | — |
| Comments | stable emulsion | stable emulsion | unstable | — | stable emulsion |

[1]Emulsion formed but rapidly separated.

The same organopolysiloxane gel as used in the previous examples to form water-containing emulsions somewhat surprisingly demonstrates less compatibility with propylene glycol. However, stable smooth emulsions could be formed with 10%–30% propylene glycol. At 40%, an emulsion (C17) initially formed, but rapidly separated. Fine tuning of the unsaturated hydrophile nature and/or amount would be expected to provide stability even at high propylene glycol contents. In Comparative Example C18, an emulsion containing 50% propylene glycol could not be prepared. Example 19 demonstrates preparation of an emulsion containing both water and propylene glycol. For greater compatibility with propylene glycol, it may be necessary to modify the amount of gel-bound hydrophile, to use a different hydrophile, e.g., a polyoxypropylene analog of the polyoxyethylene hydrophiles of the examples, or use two or more different hydrophiles.

EXAMPLES 20–22

In a manner similar to Examples 1–8, organopolysiloxane gels were prepared employing Bimax™ AAP-10, a polyoxypropylated allyl alcohol containing nominally 10 oxypropylene moieties, and having a 2.87 weight percent "vinyl" (allyl) content. The reactions were performed in a 500 mL kettle with desiccator-capped condenser, heating mantle, metal stirrer with bearing, and temperature controller. The silicon compounds and polyether were added and stirred at 300 rpm ($5s^{-1}$) followed by addition of catalyst. The mixture was heated to 65° C. and stirred until gel formation occurred. The mixture was then held at 65° C. for an additional 30 minutes, and cooled to 40° C., at which point the inhibitor is added, and stirred in well. The mixture is then homogenized with a Turrax™ mixer. The components and product characteristics are presented in Table IV below:

TABLE 4

| Example: | 20 | 21 | 22 |
|---|---|---|---|
| Ingredients: (g) | | | |
| D5 Cyclosiloxane | 316 | 314 | 310 |
| MQ Resin 804 | 71.8 | 71.8 | 72.0 |
| Crosslinker 525 | 8.0 | 8.0 | 8.0 |
| Bimax AAP-10 | 2.5 | 4.0 | 8.0 |
| Catalyst OL | 0.20 | 0.20 | 0.20 |
| F950A | 1.20 | 1.60 | 1.60 |
| Polyglycol % by Weight | 0.617 | 1.00 | 2.00 |
| Characteristics: | | | |
| Viscosity (cP) | 84,000 | 82,500 | 24,000 |
| Appearance | creamy gel | creamy gel | liquidy |
| % H (final) | 0.0019 | 0.0026 | 0.0025 |
| Flash point, ° C. | 69.4 | 72.2 | 70.0 |
| Texture 20 mm (g) | 11 | 12 | not measured |

EXAMPLES 23–26

Ethylene glycol emulsions were prepared from organosiloxane gels of the subject invention. Ethylene glycol was slowly blended into a gel prepared in accordance with Example 8, containing 0.3 weight percent of a 10 mol adduct of ethylene oxide onto allyl alcohol. Compositions containing 10% and 30% ethylene glycol (Examples 23, 24) were very stable, exhibiting no separation even after 1 hour of centrifuging at 2000 rpm. Compositions containing 40% and 55% by weight ethylene glycol (Examples 25, 26) were also quite stable, exhibit only a small "bubble" of separated liquid after centrifuging. All the preparations exhibited a nice, creamy feel. The respective viscosities were 74,000 cPs, 123,000 cPs, 126,000 cPs, and 136,000 cPs.

EXAMPLES 27–C33

In a similar manner, emulsions were prepared from selected gels and propylene glycol, $H_2O$, or glycerine. The results are presented in Table 5.

TABLE 5

| Example | 27 | 28 | 29 | 30 | C31 | 32 | C33 |
|---|---|---|---|---|---|---|---|
| Gel from Example | 7 | 7 | 21 | 21 | 21 | 21 | 21 |
| Gel (g) | 340 | 240 | 320 | 340 g | 320 g | 340 g | 320 g |
| Water (g) | 0 | 0 | 0 | 60 g (15%) | 80 g (20%) | 0 | 0 |
| PG (g) | 0 | 0 | 0 | 0 | 0 | 60 g (15%) | 80 g (20%) |
| Glycerine (g) | 60 (15%) | 160 (40%) | 80 (20%) | 0 | 0 | 0 | 0 |
| Brookfield Visc. (spindle 6 spd 5 rpm) | 81,000 cP | 145,000 cP | 88,000 cP | 72,500 cP | — | 89,000 cP | 56,000 cP |
| Centrifuge Stability (2000 rpm, 1 h) (50 ml sample) | one droplet of separation | one droplet | 4 ml separation | no separation | separated before centrifuging | no separation | separated before centrifuging |

The above examples indicate that a wide variety of translucent and transparent, stable gels can be formed employing an unsaturated MQ resin and an Si—H functional crosslinker having Si—H functionality distributed along the crosslinker backbone. Too high a cross-linking density, regardless of the nature of the crosslinker, generally leads to crumbly products. It has been found that while the gels produced by the subject process are "stable", i.e. they do not separate into two or more phases nor do they solidify to "crumbly" or solid products, the gel "hardness" does occasionally increase somewhat over time. This increase in hardness is not a fatal flaw, but must be considered during manufacture if a gel with defined target characteristics is contemplated. This increase in gel hardness is thought to affect other gels produced through hydrosilylation reactions.

Applicants have discovered that the softness of hydrosilylation-type gels may be maintained over time if a minor, but effective amount of a hydrosilylation catalyst inhibitor is added to the formulation, preferably after initial gelation. When such inhibitors are added prior to or during hydrosilylation, the catalyst level must generally be increased somewhat, even though the hydrosilylation reaction has been largely completed at this point. Addition of such inhibitors can also generate useful gels from compositions which, if fully crosslinked, would be too highly crosslinked. Thus, the optional inhibitor component broadens the range of useful crosslinkable compositions.

The catalyst inhibitors may be selected from all hydrosilylation catalyst inhibitors available. However, because the gels are intended for cosmetic formulations, some inhibitors may not be advisable for toxicological reasons, or for customer acceptance. For example, compounds such as dodecanethiol should be avoided due to its odor. However, in perfume-laden cosmetics, or where very small amounts are used, even these inhibitors may be acceptable. The amount of inhibitor generally ranges from about 0.001 to about 2 parts by weight, preferably 0.01 part to 1 part by weight based on a total gel weight of 100 parts. More preferably, 0.1 part to 0.8 part, and most preferably 0.2 part to 0.5 parts are used. The amount is preferably sufficient such that no or only very little noticeable increase in hardness occurs over a two week period of storage at room temperature. While the inhibitors are preferably added following gelation, or following the onset of gelation, the inhibitor may be added at the same time or even before catalyst addition. Additional catalyst may be required in such cases.

The ingredients used and exemplified herein are considered individually disclosed, and may be used to exclusion of any other ingredient identified herein or not disclosed herein, so long as the necessary ingredients are employed, and a stable gel, and stable emulsion at the target hydrophilic liquid content prepared from the gel are obtained. Necessary ingredients for the organopolysiloxane gels of the present invention are a low viscosity organopolysiloxane, an unsaturation-functional MQ resin, an SiH functional crosslinker, an unsaturated, hydrosilylatable hydrophile, and a hydrosilylation catalyst. Necessary ingredients of the emulsions of the present invention are an organopolysiloxane gel as previously described, and at least one hydrophilic liquid which forms a smooth, stable emulsion in the gel at a given target concentration. In the claims, the terms "a" and "an" mean one or more than one unless indicated otherwise. By the term "incompatible hydrophilic liquid" is meant a liquid which will not form a stable emulsion at the same weight/weight concentration in a gel formed from the same components but without the incorporation of the hydrosilylatable unsaturated hydrophile component into the organopolysiloxane gel.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A stable organopolysiloxane gel which is capable of forming a stable emulsion with a hydrophilic liquid, said gel prepared by reacting a composition comprising:
   a) an organopolysiloxane resin bearing hydrosilylatable unsaturated groups;
   b) an Si—H functional organopolysiloxane crosslinker containing at least some non-terminal Si—H bound hydrogen and in excess of 5 Si—H bound hydrogens per molecule on average;
   c) an effective compatabilizing amount of hydrosilylatable unsaturated hydrophile;

in the presence of a hydrosilylation catalyst to form a gel, at least a portion of said reacting prior to gelation taking place in the presence of an oleaginous composition containing minimally 50 weight percent based on the total weight of the oleaginous composition, of a low viscosity polyorganosiloxane.

2. The organopolysiloxane gel of claim 1, wherein said hydrosilylatable unsaturated hydrophile contains a hydrophile selected from the group consisting of polyglycols, polyglycerols, oligosaccharides, hydroxyl-terminated polyoxyalkylene polyethers, carboxylate esters of hydroxyl-terminated polyoxyalkylene polyethers, lower alkanol ethers of hydroxyl-terminated polyoxyalkylene polyethers, and mixtures thereof.

3. The organopolysiloxane gel of claim 1, wherein said hydrosilylatable unsaturated hydrophile comprises a polyoxyalkylated unsaturated compound containing from three to about 50 oxyalkylene groups.

4. The organopolysiloxane gel of claim 1, wherein said hydrosilylatable unsaturated hydrophile has the formula $$CH_2=CH-CH_2-O-(R-O)_n-H$$

wherein each R independently is a $C_{1-5}$ alkylene group, and n is from 3 to 20.

5. The gel in accordance with claim 1 wherein said organopolysiloxane resin is an MQ resin, said gel prepared by reacting a composition comprising
   a) 10–30% of unsaturated MQ resin;
   b) 1–5% of Si—H functional crosslinker; and
   c) 0.1–5% of said unsaturated hydrophile;
in the presence of
   d) 88% to 60% of oleaginous composition,
all percents being % by weight relative to total weight.

6. The gel of claim 5, wherein said MQ resin has a vinyl unsaturation content of 1.0 to 2.0% by weight and is present in an amount of 15% to 20% by weight; said Si—H crosslinker is a polyorganosiloxane comprising dimethylsiloxy and hydrogenmethylsiloxy repeating units with an Si—H bound hydrogen content of 0.1 to 1.0 weight percent, said crosslinker present in an amount of from 1 to 3 weight percent by weight; and wherein said hydrophile is an oxyethylated allyl alcohol present in an amount of 0.1 to 2 weight percent; said oleaginous substance comprises minimally 80% by weight low viscosity organopolysiloxanes; and said oleaginous substance is present in an amount of 50% to about 84% based on the weight of the gel.

7. The gel of claim 1, wherein prior to, during, and/or following said reacting, an inhibitor which inhibits hydrosilylation is present.

8. The gel of claim 7, wherein the inhibitor is a sulfur-containing compound.

9. The gel of claim 1, further comprising a filler.

10. A process for the preparation of the organopolysiloxane gel of claim 1, said process comprising mixing together an unsaturated MQ resin, said Si—H functional organopolysiloxane crosslinker, said unsaturated hydrophile, and said hydrosilylation catalyst; crosslinking the mixture obtained until the mixture gels to a crosslinked gel at least a portion of said crosslinking occurring in the presence of said oleaginous substance prior to gelation; and subjecting the crosslinked gel thereby obtained to high shear mixing to form a stable creamy gel.

11. The process of claim 10, where the reaction takes place at a temperature less than 100° C., and following gelation, the temperature is maintained at higher than 50° C. for a period of at least one half hour.

12. The process of claim 10, wherein following gelation, an inhibitor of hydrosilylation is added.

13. A smooth, stable emulsion containing both a silicone gel and an incompatible hydrophilic liquid, comprising:
   a) as a silicone gel component, the organopolysiloxane gel of claim 1;
   b) an incompatible hydrophilic liquid which forms a stable emulsion with said silicone gel a).

14. A smooth, stable emulsion containing both a silicone gel and an incompatible hydrophilic liquid, comprising:
   a) as a silicone gel component, the organopolysiloxane gel of claim 2;
   b) an incompatible hydrophilic liquid which forms a stable emulsion with said silicone gel a).

15. A smooth, stable emulsion containing both a silicone gel and an incompatible hydrophilic liquid, comprising:
   a) as a silicone gel component, the organopolysiloxane gel of claim 3;
   b) an incompatible hydrophilic liquid which forms a stable emulsion with said silicone gel a).

16. A smooth, stable emulsion containing both a silicone gel and an incompatible hydrophilic liquid, comprising:
   a) as a silicone gel component, the organopolysiloxane gel of claim 4;
   b) an incompatible hydrophilic liquid which forms a stable emulsion with said silicone gel a).

17. A smooth, stable emulsion containing both a silicone gel and an incompatible hydrophilic liquid, comprising:
   a) as a silicone gel component, the organopolysiloxane gel of claim 5;
   b) an incompatible hydrophilic liquid which forms a stable emulsion with said silicone gel a).

18. A smooth, stable emulsion containing both a silicone gel and an incompatible hydrophilic liquid, comprising:
   a) as a silicone gel component, the organopolysiloxane gel of claim 6;
   b) an incompatible hydrophilic liquid which forms a stable emulsion with said silicone gel a).

19. A smooth, stable emulsion containing both a silicone gel and an incompatible hydrophilic liquid, comprising:
   a ) as a silicone gel component, the organopolysiloxane gel of claim 7;
   b) an incompatible hydrophilic liquid which forms a stable emulsion with said silicone gel a).

20. The emulsion of claim 13, wherein said hydrophilic liquid is selected from the group consisting of $C_{1-4}$ lower alkanols, $C_{2-4}$ glycols, glycerine, water, and mixtures thereof.

21. The emulsion of claim 18, wherein said hydrophilic liquid is water ethylene glycol, diethylene glycol, propylene glycol, glycerine or mixtures thereof, said hydrophilic liquid present in an amount of from 5% to about 50% based on the weight of the emulsion.

22. A cosmetic product comprising the emulsion of claim 13, and one or more cosmetically acceptable ingredients.

23. The cosmetic product of claim 22 which is not itself an emulsion.

24. The cosmetic product of claim 22, wherein said cosmetic product is selected from the group consisting of antiperspirants, deodorants, sun care preparations, after sun care preparations, moisturizers, creams, lotions, facial powder, eye powder, eye shadow, liquid foundation, liquid-to-powder foundation, lipsticks, hair conditioners, and volume enhancers.

25. A stable organopolysiloxane gel which is capable of forming a stable emulsion with a hydrophilic liquid, said gel prepared by reacting a composition comprising:

a) an organopolysiloxane resin bearing hydrosilylatable unsaturated groups;
b) an Si—H functional organopolysiloxane crosslinker containing at least some non-terminal Si—H bound hydrogen;
c) an effective compatabilizing amount of hydrosilylatable, mono-unsaturated hydrophile;

in the presence of a hydrosilylation catalyst to form a gel, at least a portion of said reacting prior to gelation taking place in the presence of an oleaginous composition containing minimally 50 weight percent based on the total weight of the oleaginous composition, of a low viscosity polyorganosiloxane.

26. A stable organopolysiloxane gel which is capable of forming a stable emulsion with a hydrophilic liquid, said gel prepared by reacting a composition comprising:
a) an organopolysiloxane resin bearing hydrosilylatable unsaturated groups;
b) an Si—H functional organopolysiloxane crosslinker containing at least some non-terminal Si—H bound hydrogen;
c) an effective compatabilizing amount of hydrosilylatable unsaturated hydrophile;

in the presence of a hydrosilylation catalyst to form a gel, said reacting taking place in the presence of 75 to 85 weight percent of a low viscosity polyorganosiloxane.

* * * * *